United States Patent [19]

Cutchens et al.

[11] 4,395,573

[45] Jul. 26, 1983

[54] PRODUCTION AND SEPARATION OF AMINES

[75] Inventors: Charles E. Cutchens; Marion J. Mathews, III; Mark S. Sowell, III, all of Pensacola, Fla.

[73] Assignee: Monsanto Company, St. Louis, Mo.

[21] Appl. No.: 324,189

[22] Filed: Nov. 23, 1981

[51] Int. Cl.³ .................... C07C 87/14; C07C 87/16
[52] U.S. Cl. .................................. 564/492; 564/491; 564/493
[58] Field of Search .................... 564/492, 491, 493

[56] References Cited

U.S. PATENT DOCUMENTS 3,821,305  6/1974  Bartalini et al. ................... 564/492
4,053,516 10/1977  Hammerstrom et al. ... 564/492 UX
4,247,481  1/1981  Campbell et al. ................... 564/492

*Primary Examiner*—Paul F. Shaver
*Attorney, Agent, or Firm*—Thomas Y. Awalt, Jr.

[57] ABSTRACT

In the production of hexamethylenediamine from adiponitrile an inorganic base is used to facilitate separation of Raney nickel catalyst and crude hexamethylenediamine.

6 Claims, 1 Drawing Figure

U.S. Patent    Jul. 26, 1983    4,395,573
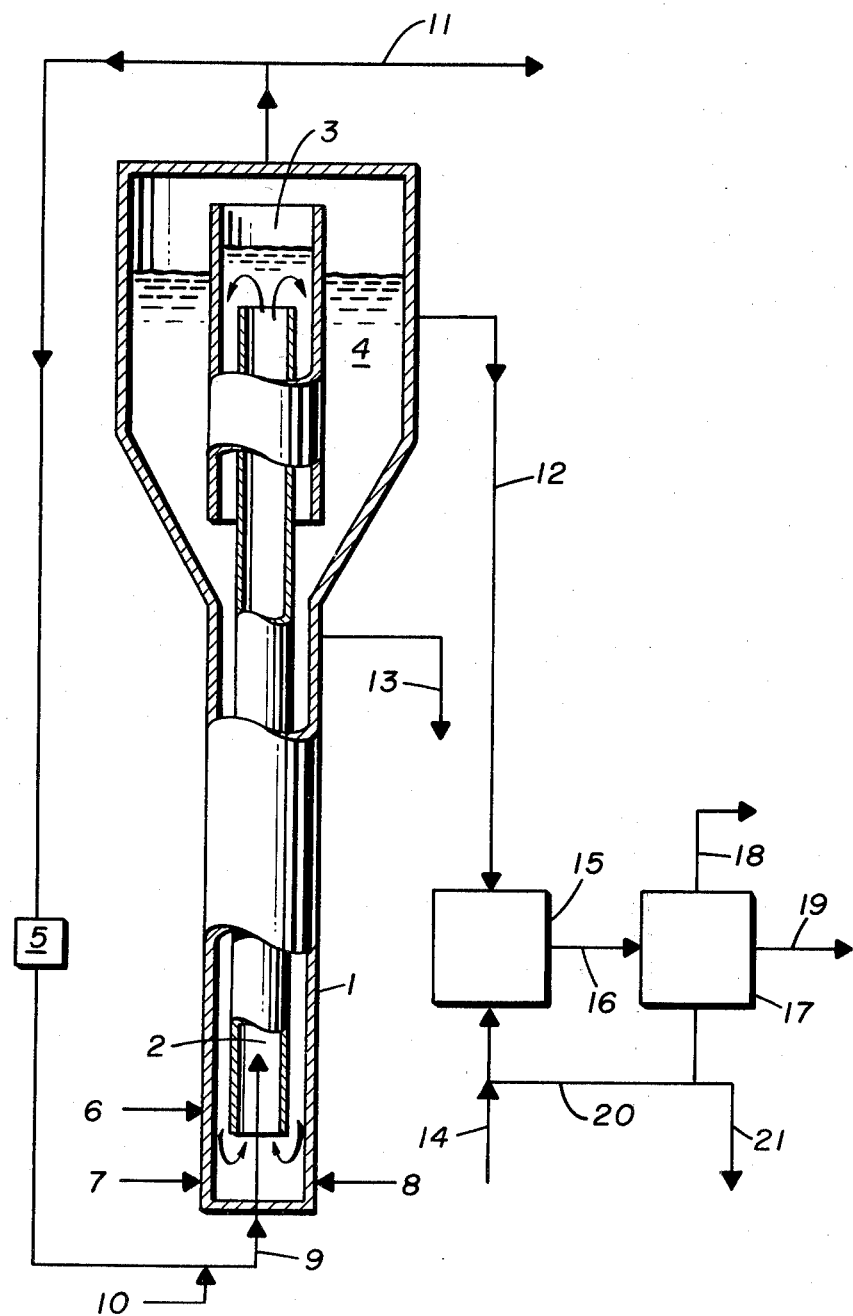

PRODUCTION AND SEPARATION OF AMINES

FIELD OF THE INVENTION

The invention relates to a process for the production of an amine such as hexamethylenediamine from a nitrile such as adiponitrile where the nitrile is hydrogenated under pressure in the presence of a Raney nickel catalyst, the reaction being conducted in a reactor from which is discharged a product stream containing both the amine and Raney nickel catalyst.

BACKGROUND OF THE INVENTION

It is well known that amines such as hexamethylenediamine can be produced by the catalytic hydrogenation of nitriles such as adiponitrile in the presence of Raney catalysts.

One such process is described in U.S. Pat. No. 3,821,305, in which hydrogenation is conducted in liquid phase at pressures of from 20–50 atmospheres and temperatures of 60°–100° C. in the presence of finely divided Raney catalyst and an inorganic base. Hydrogen and adiponitrile are fed into a liquid reaction medium consisting of hexamethylenediamine, water, the inorganic base, and the catalyst, in which medium the content of base is maintained in the range of 0.2–12 moles per kilogram of catalyst, while the content of water is maintained in the range of 2–130 moles per mole of the base.

The process discharge stream in the above described process contains both Raney catalyst and the product hexamethylenediamine, from which it is desirable to recover substantially pure hexamethylenediamine by distillation, and to recycle the Raney catalyst.

In order to passify the Raney nickel catalyst so as to prevent decomposition of the product hexamethylenediamine it is known to charge to the product discharge stream an inorganic base. The utilization of this inorganic base to assist in the separation of the product hexamethylenediamine would constitute a significant improvement in the art and is an object of this invention.

SUMMARY OF THE INVENTION

Briefly, the invention is an improvement in a process for the production of an amine such as hexamethylenediamine from a nitrile such as adiponitrile where the nitrile is hydrogenated under pressure in the presence of a Raney nickel catalyst continuously in a reactor thereby to produce an amine which is discharged in a stream from which is recovered both hexamethylenediamine and Raney nickel catalyst. An inorganic base is charged to the process discharge stream in order to passify the Raney nickel catalyst and prevent catalytic decomposition of the amine. According to this invention, the inorganic base is mixed with the process discharge stream to form a separable mixture, then the separable mixture is fed to a decanter where, in the course of decantation, hexamethylenediamine is removed from the top, the Raney nickel catalyst is intermittently purged from an interface between the amine and the inorganic base, and the inorganic base is removed from the bottom and recirculated to the process discharge stream.

According to this invention, the catalyst level in crude hexamethylenediamine can be reduced from typical ranges of 50–200 ppm to levels below 15 ppm in the decantation step.

DETAILED DESCRIPTION OF THE INVENTION

While the invention is applicable to any process for the production of an amine from a nitrile in which a Raney nickel catalyst is employed, the invention will be described in the context of a preferred process for such production.

The process for the production of the hexamethylenediamine is preferably carried out in pressures of 20–50 atmospheres in temperatures of 60°–100° C., by feeding molecular hydrogen and adiponitrile into a liquid reaction medium containing, along with the hexamethylenediamine produced, water, sodium hydroxide and a finely divided Raney catalyst dispersed in the liquid components of the reaction medium. The catalyst, which may be Raney nickel, or Raney nickel containing small amounts of other metals such as chromium, loses all or most of its activity during hydrogenation. In order to maintain a given level of catalytic activity with the catalytic mass, it is necessary for the catalyst in the reaction medium to be gradually replaced. This replacement is effected by feeding fresh catalyst to the reaction vessel and removing a quantity of reaction medium which contains an amount of catalyst equal to that supplied. The feed catalyst may consist of a mixture of fresh catalyst and of recycled catalyst. Recycled catalyst is catalyst that has been washed prior to re-use.

The reaction medium preferably contains:

(1) a quantity of catalyst in excess of 1 part, by weight, per 100 parts of liquid reaction medium (hexamethylenediamine, water and sodium hydroxide), the upper limit depending solely on the fluidity of the reaction medium; the preferred range is from 3 to 35 parts per 100 parts by weight of the liquid reaction medium;

(2) a quantity of sodium hydroxide in the range of 0.2 to 12 moles per kilogram of catalyst and preferably between 1 and 3 moles per kilogram of catalyst;

(3) a quantity of water in the range of 2 to 130 moles per mole of sodium hydroxide and preferably between 7 and 70 moles per mole of sodium hydroxide.

Substantially similar results in the production of the amine can be obtained by using, instead of sodium hydroxide, a hydroxide of any other of the alkali metals. Throughout the following description, however, reference will be made to the preferred sodium hydroxide.

The liquid part of the reaction medium, under the starting conditions already specified, and within the preferred range of ratio of water to sodium hydroxide, consists of two phases. One phase, amounting to 0.5–5.0 parts per 100 parts of the other phase, consists of an aqueous solution of sodium hydroxide whose concentration is in the range of 25 to 55 percent by weight. The other phase consists of hexamethylenediamine containing water and small amounts of sodium hydroxide. The aqueous solution of sodium hydroxide, which is the heavier phase, contains most of the catalyst.

The equipment for continuous operation of the process is of conventional type. An example of this, which is not limitive of the invention, is shown in the accompanying drawing. The equipment consists essentially of a vertical tubular reaction vessel, 1, provided inside with an injection device, 2, such as to promote the agitation of the reaction medium resulting from hydrogen flow, and at the top with containers, 3 and 4, which enable the separation of the gas from the liquid and the drawing off from the reaction vessel of the hydrogenated product having a low content of catalyst thus making it possible to maintain in the reaction vessel relatively high concentrations of catalyst—for example, 10-20 parts of catalyst per 100 parts by weight of liquid reaction medium.

The equipment also includes a gas re-cycling pump, 5, and pipes for feeding the reaction vessel with adiponitrile 6, aqueous solution of sodium hydroxide 7, catalyst 8, and hydrogen, 9. The hydrogen consumed is replaced by feeding fresh hydrogen through pipe 10.

Part of the gas is vented through pipe 11, the purpose of this release being to maintain the hydrogen content in the re-cycled gas above a given value.

Hexamethylenediamine is discharged through pipe 12.

Pipe 13 is used for removing an amount of reaction medium whose catalyst content is equivalent to the amount supplied through pipe 7. In this way, the concentration of catalyst in the reaction medium remains constant.

The inorganic base may be introduced to the product discharge stream at any convenient point.

According to the preferred embodiment the inorganic base is charged to mixer 15 through pipe 14. The product discharge stream is transmitted through pipe 12 to mixer 15 from which it is transmitted through pipe 16 to decanter 17. Crude hexamethylenediamine is decanted off through pipe 18. A layer of catalyst is removed intermittantly at pipe 19 and the settled inorganic base is returned to mixer 15 through pipe 20. Equilibrium between the hexamethylenediamine and the inorganic base can be controlled by fresh addition and by purge of inorganic base. An optional purge pipe 21 is shown although not considered essential to this invention. Wherever elimination of water in the system is desired an optional flasher (not shown) may be employed between the decanter and the mixer. If the level of inorganic base in decanter 17 decreases, this indicates extraction of water and the inorganic base into the hexamethylenediamine phase; and increasing the concentration of the inorganic base is the desired corrective action. Conversely, the concentration of the inorganic base can be decreased if the level of inorganic base is building. The concentration of inorganic base can be controlled by addition of concentrated caustic at 14 or by purging at 21.

As will be seen in the examples, temperatures of the order of 70°-90° have been found to be satisfactory. Variations in temperatures within this range have no effect on catalyst removal. Mixture weight ratios of sodium hydroxide to hexamethylenediamine from 0 to 0.39 have been tested, and although lesser amounts of sodium hydroxide added to the process discharge stream do result in catalyst passivation and easier catalyst removal than where there is no sodium hydroxide, ratios greater than 0.1 resulted in more efficient catalyst removal.

EXAMPLES

To a process discharge stream of the type shown in the FIGURE was charged sodium hydroxide in the amount shown, and the stream was subjected to mixing and decantation as described above, at temperature ranges shown at Table I. Catalyst measurements were taken in both the crude hexamethylenediamine (pipe 12) and from the decanted crude hexamethylenediamine stream (pipe 18). The results are as shown in Table I.

TABLE I

Decanter Settling Time = 5 minutes.
Decanter operated at atmospheric pressure.

| Mixture Ratio NaOH/HMD, wt/wt | Temperature °C. | Catalyst in Crude HMD, ppm | Catalyst in Clarified Crude HMD ppm |
|---|---|---|---|
| 0.0 | 90 → 80 | 70 | 70 |
| 0.17 | 90 → 80 | 70 | 5 |
| 0.11 | 70 | 276 | <1* |
| 0.02 | 70 | 45 | 14 |
| 0.05 | 70 | 614 | 12 |
| 0.25 | 75 | 125 | 8 |
| 0.08 | 90 → 75 | 52 | 9 |
| 0.16 | 90 → 76 | 52 | 5 |
| 0.39 | 90 → 75 | 52 | 6 |
| 0.16 | 90 → 75 | 52 | <1* |
| 0.16 | 80 → 72 | 52 | <1* |
| 0.16 | 70 → 68 | 52 | <1* |
| 0.21 | 60 | 96 | 13 |
| 0.21 | 75 | 96 | 5 |
| 0.21 | 90 | 96 | 11 |

*<1 is undetectable.

We claim:

1. In a process for the production of an amine from a nitrile where the nitrile is hydrogenated under pressure in the presence of a Raney nickel catalyst continuously in a reactor thereby to produce the amine which is discharged in a stream from which is recovered both the amine and the Raney nickel catalyst, where the Raney nickel catalyst is passivated by charging to the process discharge stream comprising the product amine and the Raney nickel catalyst an inorganic base, and where the product amine is subsequently separated from the Raney nickel catalyst and the inorganic base, the improvement wherein the separation is characterized by mixing the inorganic base with the process discharge stream to form a separable mixture, decanting the separable mixture so as to remove the upper layer comprising substantially catalyst-free amine from the lower layer comprising the aqueous solution of the inorganic base, and intermittently purging Raney nickel catalyst at the interface of the amine phase and the inorganic base phase.

2. The process of claim 1 wherein the nitrile is adiponitrile and the amine is hexamethylenediamine.

3. The process of claim 1 wherein the inorganic base is sodium hydroxide.

4. The process of claim 1 which the temperature of the product stream in the decanter during decantation was in the range of 70°-90° C.

5. The process of claim 1 wherein the weight ratio of inorganic base to the amine is about 0.01-0.39.

6. In a process for the production of hexamethylenediamine from adiponitrile where the adiponitrile is hydrogenated under pressure in the presence of a Raney nickel catalyst continuously in a reactor thereby to produce hexamethylenediamine which is discharged in a stream from which is recovered both the hexamethylenediamine and the Raney nickel catalyst, where the Raney nickel catalyst is passivated by charging to the process discharge stream comprising the product hexamethylenediamine and the Raney nickel catalyst sodium hydroxide at a weight ratio of sodium hydroxide to hexamethylenediamine of about 0.1-0.39, and where the product hexamethylenediamine is subsequently separated from the Raney nickel catalyst and the sodium hydroxide, the improvement wherein the separation is characterized by mixing the sodium hydroxide with the process discharge stream, decanting the process discharge stream so as to remove the upper layer comprising essentially catalyst-free hexamethylenediamine from the lower layer comprising the aqueous solution of the sodium hydroxide and intermittently purging Raney nickel catalyst at the interface of the hexamethylenediamine phase and the sodium hydroxide phase.

* * * * *